United States Patent

Joshi et al.

[11] Patent Number: 5,954,268
[45] Date of Patent: Sep. 21, 1999

[54] FLUID DELIVERY SYSTEM

[76] Inventors: Ashok V. Joshi, 4552 Thousand Oaks Dr., Salt Lake City, Utah 84124; John H. Gordon, 2090 Yale Ave., Salt Lake City, Utah 84108; Giorgio di Palma, 12657 S. Bridgewood La., Draper, Utah 84023; John I. McEvoy, 11435 S. Player Rd., Sandy, Utah 84092; Truman Wold, 923 Greenwood Ter., Salt Lake City, Utah 84105

[21] Appl. No.: 09/139,446

[22] Filed: Aug. 25, 1998

Related U.S. Application Data

[63] Continuation of application No. 08/804,286, Mar. 3, 1997.

[51] Int. Cl.$^6$ ..................................................... A24F 25/00
[52] U.S. Cl. ............................... 239/34; 239/111; 428/24
[58] Field of Search .......................... 222/386.5; 239/34, 239/53–56, 211; 428/24, 34.1, 26, 905

[56] References Cited

U.S. PATENT DOCUMENTS

| | | | |
|---|---|---|---|
| 1,701,032 | 2/1929 | Dubray | 428/24 X |
| 2,559,091 | 7/1951 | Reasenberg | 239/309 X |
| 4,175,704 | 11/1979 | Cohen | 239/331 X |
| 4,860,953 | 8/1989 | Hsien | 239/34 |
| 5,063,485 | 11/1991 | Harris | 428/24 X |
| 5,423,454 | 6/1995 | Lippman et al. | 222/386.5 X |
| 5,776,561 | 7/1998 | Lindauer | 239/34 X |

*Primary Examiner*—Kevin Weldon
*Attorney, Agent, or Firm*—Factor and Shaftal

[57] ABSTRACT

A fluid delivery apparatus includes a housing having an open end and an interior surface. The interior of the housing defines a cavity within the housing. The cavity, in combination with a piston-like member, defines a reservoir for containing a fluid (e.g. such as an aromatic or other solvent or a solvent in which has been dissolved an aromatic substance). The piston has a port, and fits in piston-like arrangement within a cylinder contained within the housing. The piston moves within the housing, and movement of the piston acts to displace fluid from the port upon contraction of the reservoir (e.g. when the annular piston is driven into the device). Preferably, a fluid tight membrane covers the housing's open end. The apparatus also preferably further includes a conduit to transport fluid from the housing of the reservoir. The conduit has, on a first end, an exterior circumference sized and shaped to interact with the port of the annular member. On the second end of the conduit is preferably associated a sponge, wick or equivalent fragrance dispenser.

18 Claims, 3 Drawing Sheets

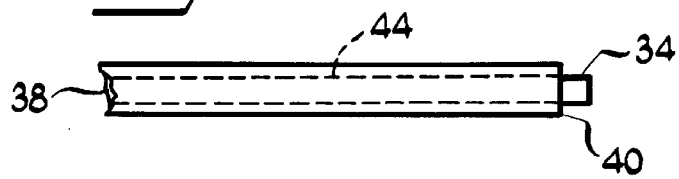
Fig 5
Fig 6
Fig 7
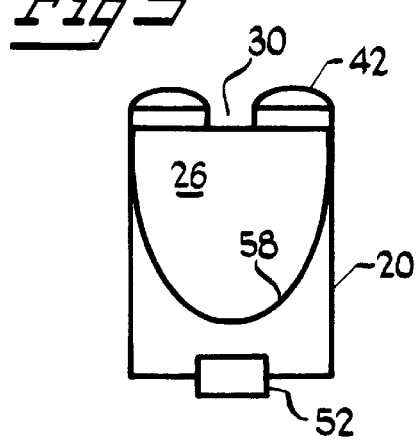
Fig 9
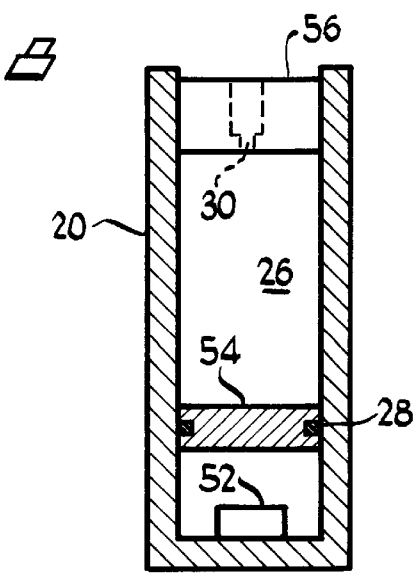
Fig 8

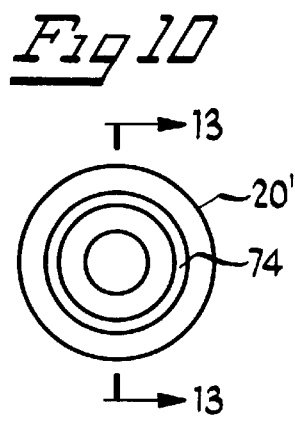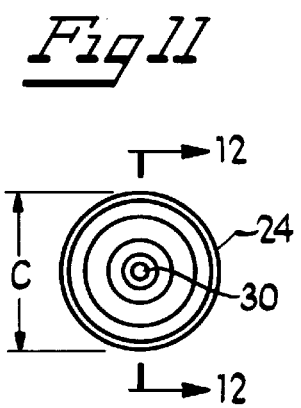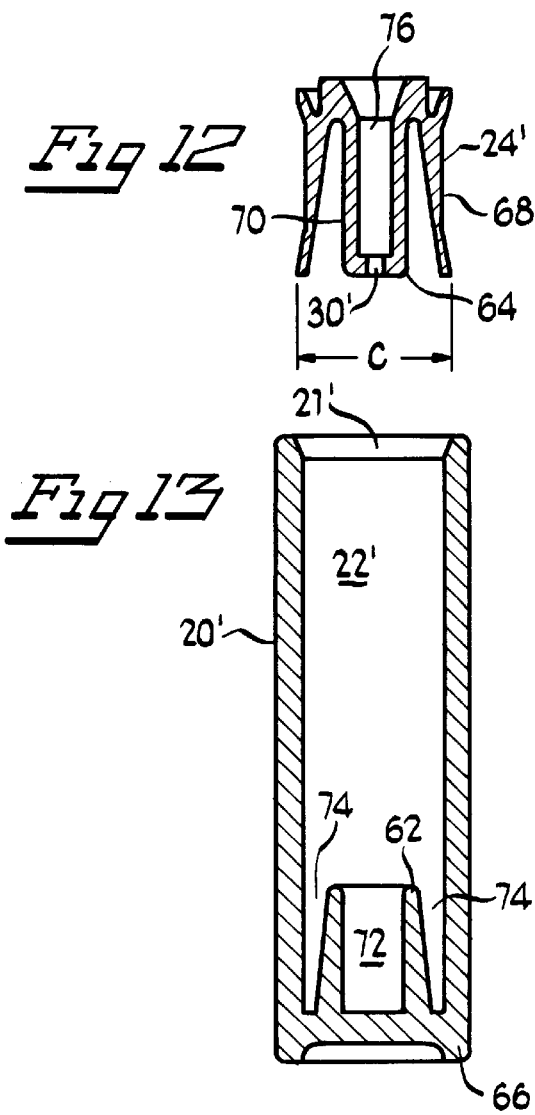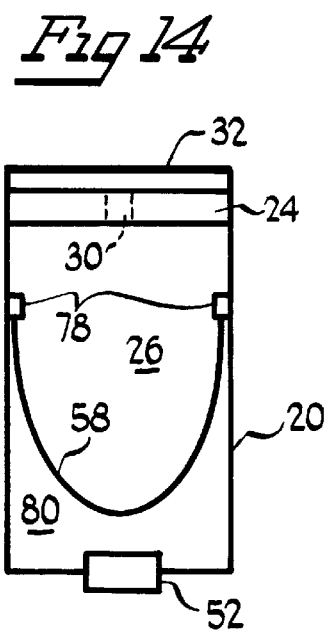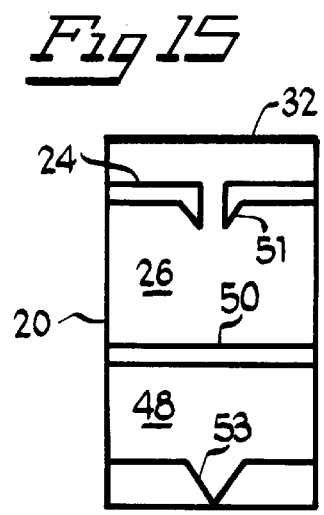

FLUID DELIVERY SYSTEM

This application is a continuation of Ser. No. 804,286 filed Mar. 3, 1997.

TECHNICAL FIELD

This invention relates generally to fluid delivery systems, and more specifically, to a fragrance delivery pump system for artificial flowers or the like.

BACKGROUND

U.S. Pat. No. 5,437,410 to Babasade (Aug. 1, 1995) discloses a passive fragrance dispenser which uses a wick within a hermetically sealed tube. The wick serves to deliver fluid from a fragrance dispensing reservoir to a fragrance diffuser. While adequate for some applications, such a passive fragrance dispenser has some drawbacks. For instance, since the device relies on capillary action to deliver the fluid, it may take some time for the fragrance containing solution to reach the emanator. Unfortunately, capillary action or wicking devices cannot effectively raise the fragrance or other fluid more than about a foot against gravity. Also, in the case of Babasade, a separate wick is incorporated within a conduit to draw fluid with one end from the fragrance dispensing reservoir and deliver it to the other end which can serve as a fragrance diffuser, which can add to manufacturing costs.

DISCLOSURE OF THE INVENTION

The invention includes a device for delivering a fluid which device includes a housing having an open end and an interior surface (e.g. an open canister). The interior of the housing defines a cavity within the housing. The cavity, in combination with a slidably associated piston-like member, defines a compressible reservoir for containing the fluid to be delivered. As hereinafter more thoroughly described, the fluid can contain just a solvent (e.g. a solvent such as a lower alcohol or water), or can contain both solvent and a separate aromatic or useful substance. The piston-like member has a port and an exterior surface having an outer circumference less than the inner circumference of the first cavity within which the piston-like member is associated. The piston-like member moves within the housing in piston-like arrangement, and the member may be moved within the cavity of the housing. Movement of the piston-like member acts to expel or dispense fluid from its port by contracting the volume of the fluid reservoir (e.g. when the annular piston is driven into the cavity of the device). The piston-like member may be pre-packaged within the housing, or it may be pre-associated with a conduit (such as the open end of a conduit-containing artificial flower stem) for transporting the fragrant fluid to an emanator or similar device. Preferably, a fluid tight membrane covers the housing's open end.

In another embodiment of the invention, a fluid delivery apparatus includes a housing having an open end and an interior surface defining a cavity. The open end has an annular member placed therein, and the aperture of the annular member defines a port. A separate piston is associated with the housing and may be moved within the cavity of the housing. An aromatic fluid is contained within a reservoir defined by the cavity and the piston. A chamber is in fluid communication with the piston and further contains means for delivering a gas to the chamber, whereby when gas is delivered to the chamber, the piston moves, thus compressing the contents of the reservoir and delivering fluid from the port.

The invention further includes a fluid delivery device having a housing with an open end and an interior surface defining a first cavity; a fluid-tight bladder having a first side and a second side. The bladder is sealedly positioned within the housing to define (on its first side) a reservoir. Fluid is contained within the reservoir defined by the bladder, and means exists for delivering a gas to the second side of the bladder. When gas is thus delivered, the bladder contracts, thus the reservoir compresses and fluid is displaced from the open end.

The apparatus preferably further includes a conduit to transport fluid from the housing of the reservoir. In one embodiment, the conduit has, on a first end, an exterior circumference sized and shaped to interact with the port of the annular member. In another embodiment, the conduit is pre-associated with the annular member, or is integrally formed with the annular member. On the second end of the conduit is preferably associated a sponge, wick or equivalent fragrance dispenser.

The invention allows one to raise fluid at any desired height immediately. In contrast to wicking devices which take a substantial amount of time to raise the fluid against gravity, the herein described pump yields instant action.

BRIEF DESCRIPTION OF THE FIGURES

In the drawings, which depict presently preferred embodiments of the invention and in which like reference numerals refer to like parts in different views or embodiments:

FIG. 5 is a break away side view of a conduit for use with the invention.

FIG. 6 is a front view of a cross-section of one embodiment of a conduit for use with the invention.

FIG. 7 depicts an artificial flower with fluid conducting conduit for use with the invention.

FIG. 8 depicts an enlarged, cross-sectional side view of an alternative embodiment of the invention.

FIG. 9 depicts an enlarged, cross-sectional side view of an alternative embodiment of the invention.

FIG. 10 depicts an enlarged, top view of a preferred canister according to the invention.

FIG. 11 depicts an enlarged, top view of a plunger for use with the canister of the preceding figure.

FIG. 12 depicts an enlarged, cross-sectional view of the plunger of FIG. 11, taken along section line 12—12.

FIG. 13 depicts an enlarged, cross-sectional view of the canister of FIG. 10, taken along section line 13—13.

FIG. 14 depicts a cross-sectional side view of an alternative embodiment of the invention.

FIG. 15 depicts a cross-sectional side view of an alternative embodiment of the invention.

BEST MODE OF THE INVENTION

Figure 1:
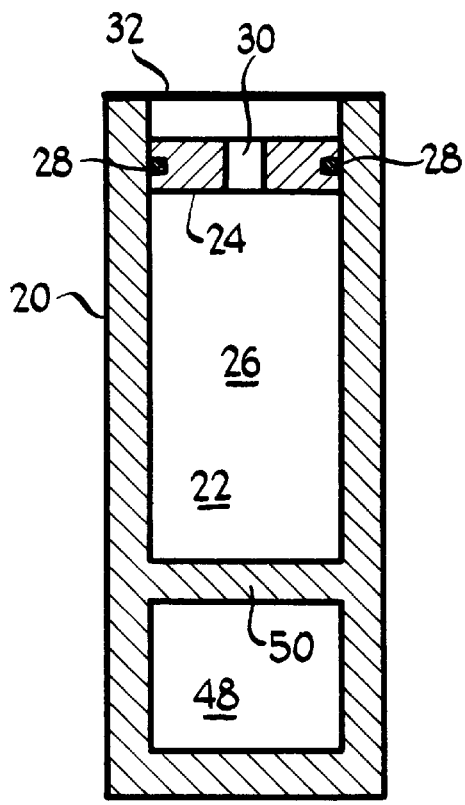
FIG. 1 depicts an enlarged cross-sectional view of one embodiment of the invention.

As shown in FIG. 1, in a preferred embodiment of the invention, the housing 20 is a cylindrical member made of a plastic or similar material. Within a first cavity of the housing 22, is placed a moveable member such as annular piston 24. The piston 24 together with the interior walls of the cylinder define a reservoir 26 for containing a fluid.

The fluid will typically be a beneficial agent, and will typically include a solution of an aromatic solvent (e.g. liquid incense), a solvent which evaporates at room temperature (e.g. a lower alcohol such as ethanol, methanol, isopropanol, acetone, water, or mixtures thereof), or an aromatic substance (e.g. an aromatic liquid such as cologne, perfume, mint oil, rose oil, rose water). Other beneficial agents for use with the invention include insect and other pest repellents, insecticides, and disinfectants.

Figure 3:
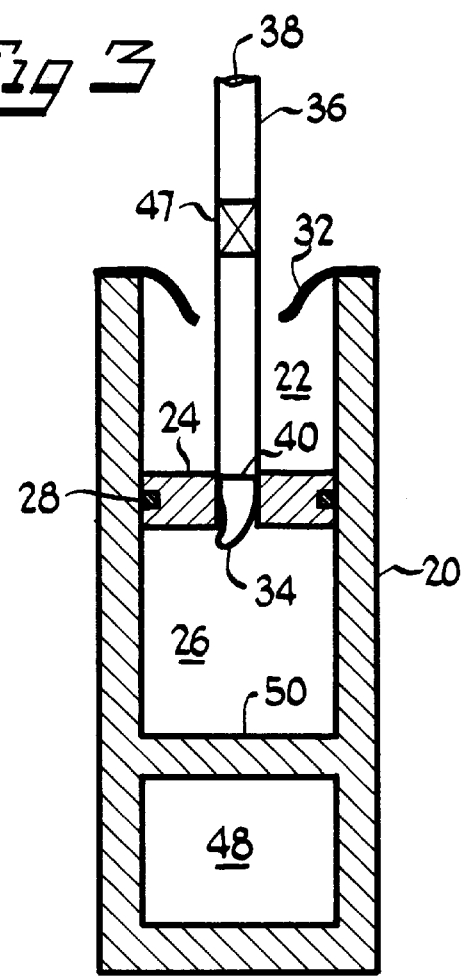
FIG. 3 depicts an enlarged cross-sectional view of an embodiment according to the previous two figures, wherein the device has been associated with an artificial flower stem,,and actuated.
Figure 2:
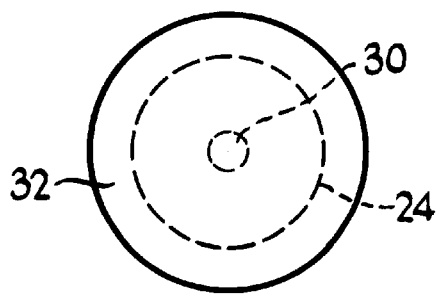
FIG. 2 depicts a top view of the preceding figure.
Figure 4:
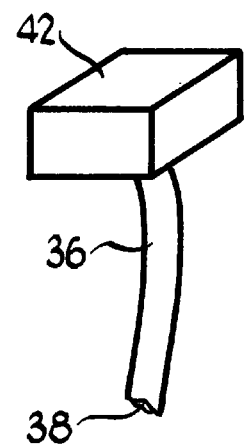
FIG. 4 depicts a conduit with associated fragrance emanator or fragrance disperser.

As depicted in FIGS. 1–3, an appropriately sized rubber O-ring 28 may be associated with the piston 24 placed between the piston and the interior wall of the cylindrical housing 20 in a groove or indentation formed in the piston. This O-ring assists in forming a fluid tight seal about the reservoir to contain the fluid until use, while still not interfering with the ability of the piston to slide within the cylindrical member.

The piston 24 has an aperture 30 extending therethrough (e.g. by molding or boring) in its approximate center which extends from the top of the piston to the reservoir. As more thoroughly described herein, upon actuation of the system, fluid contained within the reservoir passes through the aperture 30 to an environment outside of the device, for example, through an associated conduit member.

As depicted in FIGS. 1 & 2, a fluid tight membrane 32 (e.g. metallized plastic film, plastic film, aluminum foil or an equivalent film-like material) may cover the open end of the cylinder 20 until ready for use. The membrane 32 helps to contain the fragrant fluid within the device, and to prevent its premature evaporation. Although FIG. 2 depicts a circular device (in cross-section) the device may have other cross-sectional shapes such as triangular, rectangular, oval, star-shaped, etc.). In which case, the outer cross-section of the piston will be like shaped so as to slidably interact with the housing in piston/cylinder-like fashion.

In use, the tip 34 of an artificial flower stem 36 (or similar conduit-type device) is preferably used to puncture the membrane 32 (FIG. 3). As shown, the tip portion 34 of the conduit 36 is sized and shaped to be received within the aperture 30 of the piston 24 and preferably is of a length that extends beyond the bottom of the piston. An extra flange, receptacle, or lip may be associated with the piston to maintain the stem's positioning or, alternatively, the piston may be thicker than that depicted in FIGS. 1–3 to maintain the stem's position (see, e.g. FIG. 12). The tip 34 is typically one open end of a hollow material capable of transmitting the fluid contained within the reservoir (e.g. aluminum, copper, or plastic tubing) which allows fluid to enter the interior 38 of the conduit 36, and is sufficiently rigid and strong to pierce the membrane 32. This hollow portion extends throughout the conduit 36, although the conduit may have a one-way valve 47 placed therein to decrease draining of fluid from the stem. The stem is typically encased with a colored polymeric material 46 such as a flexible plastic. The exterior of the conduit preferably forms a lip or flange 40 with the tip 34, which flange 40 interacts with the piston 24 to drive the piston towards the bottom of the housing when the conduit 36 is driven in the same direction by an user. This movement of the piston 24 compresses the reservoir 26 and displaces fluid contained therein through the aperture 30 into the lumen of the tip 34 and into the interior 38 of the conduit 36.

The fluid is thus transferred from one end of the conduit to the other end (or other ends). The other end of the conduit is preferably in fluid communication with a fragrance diffuser or emanator 42 such as a sponge, gauze, cloth, or other high surface area or absorbent material, preferably associated with an artificial flower generally 43 (FIG. 7).

Although the conduit depicted in FIG. 5 is circular in internal cross-section, other orientations such as that depicted in FIG. 6 are possible. In that configuration, the lumen of the conduit is divided by walls 45 into a plurality of continuous chambers (i.e. in the case of FIG. 6, four continuous chambers) which help improve distribution of the liquid. A total surface area of the cross-sectional area of about 0.0030 square inches is presently preferred, although other sizes (e.g. from about 0.0015 to about 0.0090 square inches) will work, and several other dimensions can be determined by one of skill in the art.

As shown in FIGS. 1 & 3, the housing 20 preferably also includes a second chamber or cavity 48. The second cavity is preferably separated from the first cavity 26 by a fluid impermeable membrane or wall 50 with or without an aperture similar to that formed in the moveable member 30. This second cavity 48 preferably contains a fluid such as air which may be slightly pressurized. This fluid impermeable membrane 50 may be fractured by the extended tip of the conduit when the piston is driven to the bottom of the cavity 22, and the air contained therein used to evacuate the contents of the conduit.

Alternatively, and as depicted in FIG. 15, the piston 24' can be modified to have a puncturing member 51 which is used to fracture the wall 50. In such a case, the bottom of the housing can have means 53 for receiving the puncturing member.

An alternative embodiment of the device is depicted in FIG. 8. In that embodiment, an electrochemical gas generating cell 52 or other gas generating or pumping device is in fluid communication with the bottom of the housing 20. A piston member 54 is placed within the housing above the electrochemical cell 52. The reservoir 26 rests above the piston member 54 in a slidable relationship. A second annular member 56 is affixed to the interior of the housing. This second annular member acts to support the encased conduit stem of an artificial flower. When gas is generated by the electrochemical cell 52, the piston 54 arises, compressing the reservoir 26 thus driving any fluid contained within the reservoir out of the aperture 30 in the second annular member (much as previously described with regard to the piston member 24 of FIG. 1).

Electrochemical cells capable of generating gases such as oxygen ($O_2$), hydrogen, nitrogen, halogen (e.g. $Cl_2$, bromine, iodine), carbon dioxide, and mixtures thereof are known. See, e.g., U.S. Pat. Nos. 4,402,817 and 4,522,698 to Maget (Jun. 11, 1985) which describe electrochemical cells. Preferred electrochemical cells for use with the invention include metal electrolyte electrochemical cells capable of generating hydrogen or oxygen. Electrochemical cells include solid polymer electrolyte-based oxygen or hydrogen generators, zinc-air type hydrogen gas generating batteries (see, e.g., U.S. Pat. No. 5,245,565 to Winsel (Sep. 7, 1993) or U.S. Pat. No. 4,023,648 to Orlitzky et al.), $Cu(OH)_2$ or carbonate-based oxygen generating cells, NaSiCON-based $CO_2/O_2$ generating cells (see, International Application No. PCT/US96/04359 (International Publication No. WO 96/30563, published Oct. 3, 1996) to Ceramatec, Inc. (corresponding to co-owned, co-pending U.S. patent application Ser. No. 08/413,635 filed on Mar. 30, 1995, now U.S.

Pat. No. 5,593,552), or nitrogen generating batteries (see, e.g., U.S. Pat. No. 5,427,870 (Jun. 27, 1995)). The contents of all of these referenced patents and patent application are incorporated by this reference. Some cells require separate power sources (e.g. a battery), while others are self-powered.

As described in U.S. Pat. No. 4,902,278, a voltage gradient established across the electrochemical cell ionizes an electrochemically active material (e.g. atmospheric oxygen) at an electrode, transporting the ions through an electrolytic membrane to the other electrode and reconverts the ions to molecules of the electrochemically active material which is evolved at the second electrode. In a presently preferred embodiment, a resistor is placed between the cells' electrodes and a switch is used with the device (not shown).

FIG. 9 depicts still another embodiment of the invention wherein a moveable member (bladder 58) is sealedly attached to the open end of the cylindrical housing 20. The interior of the bladder 26 defines the fluid-containing compressible reservoir 26. The reservoir 26 is separated from an electrochemical cell 52 placed in the 5 bottom of the device. Upon actuation of the electrochemical cell 52, gas is generated, and the bladder 26 contracts, driving the aromatic fluid contained within the reservoir out of the aperture 30 and into any associated stem. While the stem tip is sharp and long enough to pierce a fluid tight membrane covering the aperture 30, it is preferably not of such a length that it can pierce or otherwise interfere with the bladder 26. In one embodiment, an emanator 42 is associated with the aperture 30 which emanator may be, for example, a toroidal sponge or ring-shaped gauze adhered to the top of the device.

Referring now to FIGS. 10 through 13, a particularly preferred embodiment of the invention is depicted. In this embodiment, the housing 20' is cylindrical, having an open end 21', and further having a cavity 22' which, in combination with an associated, corresponding crown-shaped annular member 24' (or "piston"), contains a fluid. The housing 20' has an internal cross-sectional width c which begins at the open end 21' and continues to the bottom end 66 of the housing forming a drinking glass-shaped member. The associatable annular member 24' has an outer circumference, also c (FIGS. 11 & 12), sized to slidably fit within the cavity 22' of the housing 20'. For use in driving fluid into an artificial flower stem, the housing can be made of a material having a thickness of about 1/16 to 1/4 inch.

At the bottom end 66 of the housing 20' is a fluid displacement member 62 sized and shaped to functionally interact (e.g. couple) with a corresponding portion 64 of the annular member 24' when the annular member 24' is driven to the bottom 66 of the cavity 22'. The corresponding portions 62, 64 of the components 20', 24' interact with one another so as to displace all or most of the fluid contained within the reservoir defined by the cavity 22' and the bottom portion 64 of the annular member 24' through an aperture 30' in the annular member 24'.

As the annular member 24' moves down the cavity 22' of the tubular housing 20' to its bottom 66, the crown points 68 and protruding member 70 interact with appropriately sized, shaped and placed receiving members 72, 74 positioned concentrically at the bottom 66 of the housing 20'. The circular outer crown 68 acts to contain the fragrant fluid while the crown-shaped piston member 24' is being driven down the cavity 22', while the protruding member 70 interacts with the central receiving member 72 to contain the fluid and direct it through the aperture 30'. By making the circular outer crown 68 flexible, the use of O-rings can be obviated.

A tubular artificial flower stem is sized to be placed within an appropriately sized conduit 76 in the crown-shaped plunger 68. This conduit 76 acts to maintain the artificial flower or like emanator in an upright position.

Still another embodiment of the invention is depicted in FIG. 14. This embodiment combines the gas generating elements of the device of FIG. 9 with the piston-delivery elements of the device of FIG. 1. In this embodiment, the annular piston 24 interacts with the housing 20 in the same manner as previously described with respect to FIGS. 1 through 3, however, a separate "ledge" 78, ring or other equivalent means is positioned within the cylindrical reservoir 26' to stop the downward, longitudinal movement of the piston 24 within the reservoir 26'. An electrochemical cell 52 is in fluid communication with a gas reservoir 80 defined by the remainder of the housing 20 and a bladder 58, much as previously described with respect to FIG. 9. When a conduit tip pierces the fluid-tight membrane 32, interacts with the aperture 30, and drives down the piston 24, a "bolus" of fluid is first delivered to the conduit. After which, the electrochemical cell 52 is actuated, and gas enters the gas reservoir 80, thus compressing the reservoir 26' and delivering a constant flow of fluid to the conduit. A variation of this embodiment involves integrally forming the stem with the piston or having the conduit tip itself serve as the piston (not shown).

After being apprised of the devices according to the invention, methods of making them will become readily apparent to those of skill in the art. The housing and piston may be molded from plastic (e.g. polypropylene or HDPE) or similar material. A bladder can be made of, for example, a latex or elastic plastic.

Furthermore, although the invention has been described with regard to certain preferred embodiments, various modifications can be made to the invention without departing from its spirit. For instance, the electrochemical cell of the embodiment of FIG. 8 could be associated with a balloon-like member.

What is claimed is:

1. An apparatus for delivering a fluid, said apparatus comprising:

a housing including a first end and an interior surface defining a first cavity;

a moveable member slidably associated with the interior surface of the housing, said moveable member, together with said first cavity, defining a reservoir for containing the fluid, said reservoir, upon movement of the moveable member in a first direction, being compressed;

an aperture in the movable member, and in fluid communication with the reservoir;

means for moving the moveable member in the first direction to thus compress the reservoir so as to expel fluid from said reservoir through said aperture in a second direction opposite that of the first direction; and the housing further comprises a second cavity filled with a fluid, said second cavity being fluidically isolated from said first cavity.

2. The apparatus of claim 1 wherein the fluid comprises a liquid having a fragrant aroma.

3. The apparatus of claim 1 wherein the first cavity and second cavity are separated by a frangible wall.

4. The apparatus of claim 1 wherein the fluid is selected from the group consisting of pest repellents, insecticides, water, and mixtures thereof.

5. The apparatus of claim 1 wherein said housing comprises an open, cylindrically shaped canister having a closed end and an open end.

6. The apparatus of claim 5 wherein said moveable member comprises an annular and flat piston.

7. The apparatus of claim 1, wherein the reservoir contains a fluid comprising a beneficial substance dissolved within a volatile fluid.

8. The apparatus of claim 1 further comprising a flexible hollow rod associated with the aperture of the movable member.

9. The apparatus of claim 1 further comprising an O-ring placed around an exterior surface of the movable member and sized to interact with the first cavity to contain the fluid.

10. The apparatus of claim 8 wherein the flexible hollow rod has, on a first end, an interior circumference and an, exterior circumference, the exterior circumference of the flexible hollow rod sized to interact with the aperture of the movable member in fluid-tight arrangement.

11. The apparatus of claim 8 further comprising a fragrance dispenser associated with a second end of said flexible hollow rod for dispersing the fluid expelled from the reservoir and transported through the aperture and flexible hollow rod to said fragrance dispenser.

12. The apparatus of claim 8 further comprising an emanator associated with a second end, and a one-way valve placed in the flexible hollow rod for allowing fluid to travel towards the second end, but preventing the return of said fluid to the first end.

13. An apparatus for delivering a fluid, said apparatus comprising:
  a housing including a first end and an interior surface defining first cavity and a second a cavity fluidically isolated from said first cavity by a frangible wall;
  a moveable member slidably associated with the interior surface of the housing, said moveable member, together with said first cavity and said second cavity, defining a reservoir for containing the fluid, said reservoir, upon movement of the moveable member in a first direction, being compressed;
  an aperture associated with the first end of the housing, and in fluid communication with the reservoir; and
  means for continuously and uninterruptedly displacing substantially all of the fluid in the reservoir upon single actuation of the moveable member, wherein the displacing means comprises:
    means for moving the moveable member in the first direction to thus compress the reservoir so as to expel fluid from said reservoir through said aperture in a second direction opposite that of the first direction; and
    means for piercing the frangible wall between the first cavity and the second cavity.

14. The apparatus according to claim 13 wherein the second cavity comprises a fluid under pressure.

15. An apparatus for delivering a fluid, said apparatus comprising:
  a housing including a first end and an interior surface defining a first cavity;
  a movable member slidably associated with the interior surface of the housing, said moveable member, together with said first cavity, defining a reservoir for containing the fluid, said reservoir, upon movement of the moveable member in a first direction, being compressed;
  an aperture in the movable member and in fluid communication with the reservoir; and
  means for continuously and uninterruptedly displacing substantially all of the fluid in the reservoir upon single actuation of the moveable member, wherein the displacing means comprises an electrochemical cell.

16. The apparatus according to claim 15 wherein the electrochemical cell is positioned in a second cavity fluidically isolated from the reservoir.

17. A method for displacing fluid comprising the steps of:
  providing a housing including a first end and an interior surface defining a first cavity, and a second cavity associated with the first cavity, said second and said first cavity being separated by a frangible wall;
  introducing a fluid into said housing;
  positioning a movable member into slidable association with the interior surface of the housing, to, in turn, define a reservoir for said fluid, wherein the movable member includes an aperture; and
  actuating the moveable member, to in turn, continuously and uninterruptedly displacing substantially all of the fluid in the reservoir, wherein the step of actuating the moveable member further comprising the step of piercing the frangible wall.

18. A method for displacing fluid comprising the steps of:
  providing a housing including a first end and an interior surface defining a first cavity;
  introducing a fluid into said housing;
  positioning a movable member into slidable association with the interior surface of the housing, to, in turn, define a reservoir for said fluid, wherein the movable member includes an aperture; and
  actuating the moveable member, to in turn, continuously and uninterruptedly displacing substantially all of the fluid in the reservoir, wherein the step of actuating the movable member comprises the step of activating an electrochemical cell associated with the first cavity.

* * * * *